US00PP15102P2

(12) United States Plant Patent
Olesen et al.

(10) Patent No.: US PP15,102 P2
(45) Date of Patent: Aug. 24, 2004

(54) CLIMBING ROSE PLANT NAMED 'POULYC006'

(50) Latin Name: *Rosa hybrida*
Varietal Denomination: POULyc006

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/719,709

(22) Filed: Nov. 21, 2003

(51) Int. Cl.[7] ..... A01H 5/00
(52) U.S. Cl. ..... Plt./114
(58) Field of Search ..... Plt./114

*Primary Examiner*—Anne Marie Grunberg
*Assistant Examiner*—S. B. McCormick-Ewoldt

(57) ABSTRACT

A new climbing garden rose plant which has abundant, medium pink flowers and attractive foliage. This new and distinct variety has shown to be uniform and stable in the resulting generations from asexual propagation.

1 Drawing Sheet

Botanical classification: Rosa hybrida.
Variety denomination: 'POULyc006'.

SUMMARY OF THE INVENTION

The present invention constitutes a new and distinct variety of garden rose plant which originated from a controlled crossing between a female parent 'POULsint', an unpatented variety, and the male parent, an unnamed plant. The two parents were crossed during the summer of 1994, and the resulting seeds were planted in a controlled environment in Fredensborg, Denmark. The new variety is named 'POULyc006'.

The new variety may be distinguished from its female parent, 'POULsint', by the following combination of characteristics:

1. The seed parent has very small flower size, less than 5 cm, while 'POULyc006' has larger flowers on average of 28 mm when open.
2. The seed parent has narrow and bushy growth habit, while 'POULyc006' has a broader and climbing habit.

The new variety may be distinguished from its pollen parent, an unnamed plant, by the following combination of characteristics:

1. The pollen parent flower petal color, open flower, upper surface is White Group 155D. 'POULyc006' has flower petal color, open flower, upper surface of Red Group 55B.
2. The pollen parent flower petals after opening are White Group 155D, while 'POULyc006' has flower petals after opening of Red Group 55B.

The objective of the hybridization of this rose variety was to create a new and distinct variety for garden use with unique qualities, such as:

1. Uniform and abundant light pink flowers;
2. Vigorous, but compact growth when propagated both as a budded rose and on its own roots;
3. Disease resistance.
4. Improved flowering habit. Since the variety is less apically dominant, flowers are produced evenly from lower branches to the top.

This combination of qualities is not present in previously available commercial cultivars of this type, known to the inventors, and distinguish 'POULyc006' from all other varieties of which we are aware.

As part of their rose development program, L. Pernille Olesen and Mogens N. Olesen germinated the seeds from the aforementioned hybridization during winter 1994 and conducted evaluations on the resulting seedlings in a controlled environment in Fredensborg, Denmark.

'POULyc006' was selected in the spring 1995 by the inventors as a single plant from the progeny of the aforementioned hybridization.

Asexual reproduction of 'POULyc006' by traditional budding and rooted cuttings was first done by L. Pernille and Mogens N. Olesen in their nursery in Fredensborg, Denmark in July, 1995. This initial and other subsequent asexual propagations conducted in controlled environments have demonstrated that the characteristics of 'POULyc006' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULyc006'. Specifically illustrated in FIG. 1:

FIG. 1.2; Flower bud closed, partially open bloom and ¼ open.

FIG. 1.3; Flower petals, detached;

FIG. 1.4; Sepals, receptacle, and pedicel;

FIG. 1.5; Mature leaves;

FIG. 1.6; Bare stems with thorns.

DETAILED DESCRIPTION OF THE VARIETY

Figures 1, 2, 3, 4, 5, 6:
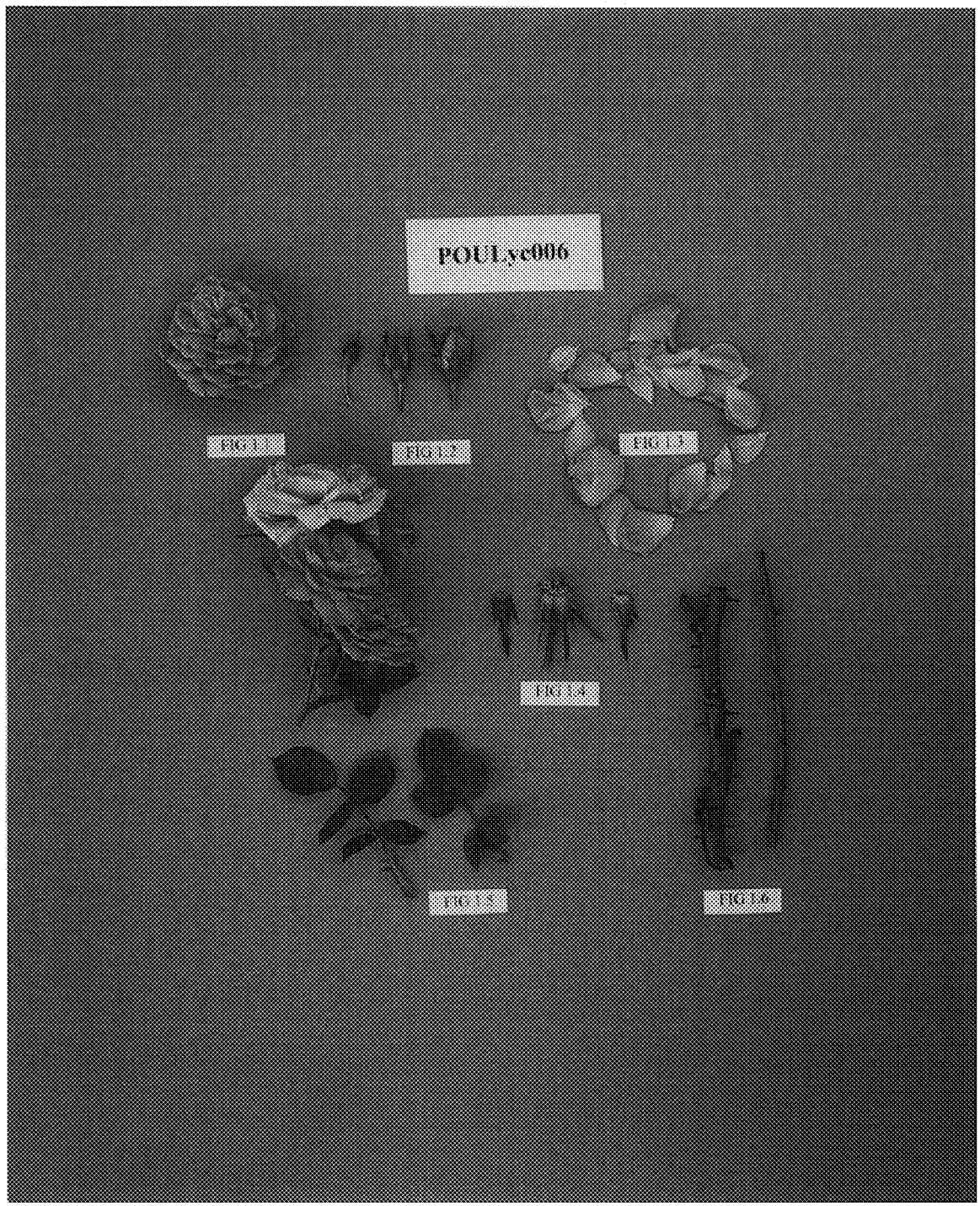
FIG. 1.1; Open flower and stem showing open flowers, and the attachment of peduncles.

The following is a description of 'POULyc006', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULover', a rose variety from the same inventors described and illustrated in U.S. Plant patent application Ser. No. 10/341,890 and dated Jan. 13, 2003, are compared to 'POULyc006' in Chart 1.

CHART 1

| | 'POULyc006' | 'POULover' |
|---|---|---|
| Bud color as sepals unfold | Petals are Red Group 55B; at ¼ opening, petals are Red Group 55B. | Petals are Red Group 55C; at ¼ opening, petals are Red Group 55C. |
| Receptacle Color | Yellow-Green Group 144B. | Yellow-Green Group 144A. |
| Outermost Petals upon opening, outer side | Red Group 55B. | Red-Purple Group 65A at petal margins. Red-Purple 65D at mid petal. |

Parents:

*Seed parent.*—POULsint.

*Pollen parent.*—An Unnamed Parent.

FLOWER AND FLOWER BUD

Blooming habit: Continuous.

Flower bud:

*Size.*—Upon opening, 20 mm in length from base of receptacle to end of bud.

*Bud form.*—Short, pointed ovoid and slightly broad based.

*Bud color.*—As sepals unfold, petals are Red Group 55B. Red Group 55B at ¼ opening.

*Sepals.*—Upper Surface: Color: Yellow-Green Group 146A. Texture: Moderately pubescent. Lower Surface: Color: Yellow-Green Group 146B. Anthocyanin: Very light, Greyed-Red Group 182A. Shape: Margins have strong foliaceous appendages on three of the five sepals. Stipitate glands are few in quantity. Size: 24 mm long by 6 mm wide.

*Receptacle.*—Surface Texture: Smooth and slightly pubescent. Shape: Urn-shaped. Size: 5 mm (h)×5 mm (w). Color: Yellow-Green Group 144B. Anthocyanin: None observed.

*Peduncle.*—Surface: Slightly pubescent. Length: 25 to 30 mm average length. Color: Yellow-Green Group 144C. Anthocyanin: Light intonations of Greyed-Red Group 182A. Strength: Somewhat strong.

*Borne.*—Multiples of 7 buds per flowering stem.

Flower bloom:

*Fragrance.*—Strong, wild rose to perfume scented.

*Duration.*—The blooms have a duration on the plant of approximately 10 to 14 days.

*Size.*—Average flower diameter is 28 mm when open.

*Form.*—Rosette with moderate petal overlap. Flowers fully open to expose reproductive organs. Shape of flower when viewed from the side: Upon opening, upper part:Flat. Upon opening, lower part:Flattened convex. Open flower, upper part: Flattened convex. Open flower, lower part: Concave.

*Petalage.*—Very double. Average range: 50–55 petals under normal conditions with 9 petaloids.

Color:

*Upon opening, petals.*—Outermost petals: Outer side: Red Group 55B. Inner Side: Red Group 55C. Innermost petals: Outer side: Red Group 55C. Inner Side: Red Group 55B to 55C.

*Upon opening, basal petal spots.*—Outermost petals: Outer side: White Group 155A. Inner side: White Group 155A. Innermost petals: Outer side: White Group 155A. Inner Side: White Group 155A.

*After opening, petals.*—Outermost petals: Outer side: Red Group 55B. Inner Side: Red Group 55C. Innermost petals: Outer side: Red Group 55C. Inner Side: Red Group 55B to 55C.

*After opening, basal petal spots.*—Outermost petals: Outer side: White Group 155A. Inner side: White Group 155A. Innermost petals: Outer side: White Group 155A. Inner Side: White Group 155A.

General tonality: On open flower Red Group 55B. No change in the general tonality at the end of the $10^{th}$ day. Afterwards, general tonality is Red Group 55B.

Petals:

*Petal reflex.*—Petals reflex somewhat.

*Margin.*—Entire with point in center of margin.

*Shape.*—Apex: Rounded. Base: Acute.

*Size.*—15 mm (l)×7 mm (w).

*Texture.*—Smooth.

*Thickness.*—Average.

*Arrangement.*—Not Formal.

Petaloids:

*Quantity.*—8–12.

*Size.*—16 mm (l)×4 mm (w).

*Color.*—Upper Surface: Red Group 55C. Lower surface: Red Group 55C.

Reproductive organs:

*Pistils.*—Length: 4 mm long. Quantity: 20 (actual count).

*Pollen.*—None observed.

*Anthers.*—Size: 1 mm long. Color: Greyed-Orange Group 163B. Quantity: 23 (actual count).

*Filaments.*—Color: Yellow-Green Group 149C. Length: 4 mm.

*Stigmas.*—Level in location to anthers. Color: Yellow-Green Group 149C.

*Styles.*—Color: Yellow-Green Group 149C. Other intonations: None.

*Hips.*—None Observed in the field nursery in Jackson County, Oreg.

PLANT

Plant growth: Vigorous, very tall climbing habit of 150–200 cm in height. Weak apical dominance causes even development of flower buds on lower and upper branches.

Stems:

*Color.*—Young wood: Yellow-Green Group 144A. Older wood: Yellow-Green Group 144B.

*Thorns.*—Incidence: 13 thorns per 10 cm of stem. Size: Average length: 6 mm. Color: Greyed-Orange Group 177A. Shape: Linear.

*Surface texture.*—Young wood: Smooth. Older wood: Smooth.

*Anthocyanin.*—None observed.

Plant foliage: Normal number of leaflets on leaves in middle of the stem: 7 leaflets.

*Compound leaf size.*—17–19 mm (l)×11–19 mm (w).

*Color.*—Mature Foliage: Upper Leaf Surface: Yellow-Green Group 146A. Lower Leaf Surface: Yellow-Green Group 146B. Juvenile foliage: Upper Leaf Surface: Yellow-Green Group 146A. Lower Leaf Surface: Yellow-Green Group 146B. Anthocyanin: None observed.

Plant leaves and leaflets:

*Stipules.*—Size: 20 mm. Color: Yellow-Green Group 144A.

*Petiole.*—Length: 30 mm. Color: Yellow-Green Group 144B. Anthocyanin: None Observed. Underneath: Thorns, few stipitate glands observed. Mildly pubescent.

*Rachis.*—Length: 25 mm. Color: Yellow-Green Group 144B. Anthocyanin: None Observed.

*Leaflet.*—Edge: Serrated. Shape: Cuspidate. Texture: Smooth. Arrangement: Odd pinnate. Venation: Reticulate. Glossiness: Glossy.

Disease resistance: Above average resistance to mildew, rust, black spot, and Botrytis under normal growing conditions in Jackson County, Oreg.

Cold hardiness: The variety 'POULyc006' has been found to be cold tolerant to USDA Cold Hardiness Zone 6.

What is claimed is:

1. A new and distinct variety of rose plant of the climbing rose class, substantially as herein illustrated and described as a distinct and novel rose variety due to its abundant light pink flowers, disease resistance, and extended period of bloom.

* * * * *

POULyc006